(12) United States Patent
Bai et al.

(10) Patent No.: US 10,441,658 B2
(45) Date of Patent: *Oct. 15, 2019

(54) OPHTHALMIC COMPOSITION

(71) Applicant: Johnson & Johnson Consumer Inc., Skillman, NJ (US)

(72) Inventors: Mingqi Bai, Jacksonville, FL (US); Kenneth T. Holeva, Ponte Vedra Beach, FL (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/279,129

(22) Filed: Feb. 19, 2019

(65) Prior Publication Data

US 2019/0184016 A1 Jun. 20, 2019

Related U.S. Application Data

(62) Division of application No. 14/922,504, filed on Oct. 26, 2015, now Pat. No. 10,245,324.

(60) Provisional application No. 62/073,488, filed on Oct. 31, 2014.

(51) Int. Cl.

| A61K 47/12 | (2006.01) |
| A61K 47/34 | (2017.01) |
| A61K 47/36 | (2006.01) |
| A61K 31/728 | (2006.01) |
| A61K 47/32 | (2006.01) |
| A61K 31/715 | (2006.01) |
| A61K 9/08 | (2006.01) |
| A61K 31/785 | (2006.01) |
| A61K 31/717 | (2006.01) |
| A61K 31/77 | (2006.01) |
| A61K 9/00 | (2006.01) |
| A61K 31/78 | (2006.01) |

(52) U.S. Cl.
CPC ............ *A61K 47/12* (2013.01); *A61K 9/0048* (2013.01); *A61K 9/08* (2013.01); *A61K 31/715* (2013.01); *A61K 31/717* (2013.01); *A61K 31/728* (2013.01); *A61K 31/77* (2013.01); *A61K 31/78* (2013.01); *A61K 31/785* (2013.01); *A61K 47/32* (2013.01); *A61K 47/34* (2013.01); *A61K 47/36* (2013.01)

(58) Field of Classification Search
None
See application file for complete search history.

(56) References Cited

U.S. PATENT DOCUMENTS

| 8,119,112 B2 | 2/2012 | Xia et al. |
| 8,349,303 B1 | 1/2013 | Phillips et al. |
| 2008/0138310 A1 | 6/2008 | Ketelson et al. |
| 2008/0312182 A1 | 12/2008 | Burke et al. |
| 2009/0196845 A1 | 8/2009 | Xia et al. |
| 2009/0226498 A1 | 9/2009 | Flugge-Berendes et al. |
| 2010/0086514 A1 | 4/2010 | Liu et al. |
| 2010/0178317 A1 | 7/2010 | Burke et al. |
| 2010/0286010 A1 | 11/2010 | Xia et al. |
| 2011/0046033 A1 | 2/2011 | Zhang |
| 2011/0230424 A1 | 9/2011 | Wagenaar |
| 2011/0301250 A1 | 12/2011 | Xia et al. |
| 2011/0319502 A1 | 12/2011 | Coffey et al. |
| 2012/0070401 A1 | 3/2012 | Zhang et al. |
| 2012/0283333 A1 | 11/2012 | Xia et al. |
| 2013/0210912 A1 | 8/2013 | Davio et al. |
| 2013/0296264 A1 | 11/2013 | Davis et al. |
| 2014/0171513 A1 | 6/2014 | Seidling et al. |

FOREIGN PATENT DOCUMENTS

WO 2009120699 A2 10/2009

OTHER PUBLICATIONS

Waller, Phoebe; "7 Things You Should Never Put on or Near Your Eyes, According to the Experts"; www.bustle.com/articles/191191-7-things-you-should-never-put-on-or-near-your-eyes-according-to-the-experts; published online Oct. 26, 2016.*
PCT International Search Report, dated Jan. 20, 2016, for PCT Int'l Appln. No. PCT/US2015/057959.

* cited by examiner

Primary Examiner — Jeffrey T. Palenik

(57) ABSTRACT

The present invention relates to ophthalmic compositions for treatment of conditions in the eye. More specifically, the present invention relates to ophthalmic compositions comprising a polyquaternium compound and an anionic polymer. Methods for reducing and/or preventing the incompatibility of polyquaternium compounds with anionic polymers are also disclosed.

1 Claim, No Drawings

OPHTHALMIC COMPOSITION

RELATED APPLICATIONS

This application is a division of U.S. patent application Ser. No. 14/922,504, filed Oct. 26, 2015, currently pending, which claims priority to U.S. Provisional Patent Application Ser. No. 62/073,488, filed Oct. 31, 2014.

FIELD OF THE INVENTION

The present invention relates to ophthalmic compositions for treatment of conditions in the eye. More specifically, the present invention relates to ophthalmic compositions comprising a polyquaternium compound and an anionic polymer. Methods for reducing and/or preventing the incompatibility of polyquaternium compounds with anionic polymers are also disclosed.

BACKGROUND OF THE INVENTION

Ophthalmic solutions are sterile solutions, free from foreign particles, for instillation into the eye. In some uses, they do not have medications in them and are only lubricating and tear-replacing solutions or eye washes. In other uses, they have active ingredients in them and can be used to treat such conditions as dry eye, allergies, eye infections such as pink eye or conjunctivitis, or eye conditions such as glaucoma. They can also be used by opticians as mydriatic compositions to dilate the pupils of patients during eye examinations.

Anionic polymers such as hyaluronic acid and carboxyl vinyl polymers have been found useful in ophthalmic solutions for the treatment of eye conditions such as dry eye.

To avoid introducing infective agents into the eye, it is critical that ophthalmic solutions remain sterile in their storage containers between uses. Polyquaternium compounds are polycationic polymers that are used as surfactants in the personal care industry. Some have antimicrobial properties, and can find use as a preservative in contact lens solutions.

An issue with polyquaternium compounds is their tendency to react with anionic materials. In eye care solutions containing anionic polymers, attempts to increase the concentration of polyquaternium in the compositions results in the formation of a precipitate. The precipitate is believed to be the complexation product of anionic polymer and the polyquaternium.

There is, therefore, a need for compositions containing polyquaternium compounds with anionic polymers having reduced precipitate formation or complexation.

The present inventors have found that an amount of an organic acid effective for binding with the polyquaternium in at least a 1:1 molar ratio to inhibit, reduce or prevent the precipitation and/or complexation of the polyquaternium compound and the anionic polymer.

It is therefore an aspect of the present invention to provide compositions comprising a polyquaternium compound and an anionic polymer wherein the precipitation or complexation of the polyquaternium compound and an anionic polymer is reduced or prevented.

A further aspect of the present invention relates to composition comprising a polyquaternium compound, an anionic polymer and an effective amount of an organic acid such that precipitation and/or complexation of the polyquaternium compound and an anionic polymer is inhibited, reduced or prevented.

SUMMARY OF THE INVENTION

The present invention is directed to ophthalmic compositions for treatment of conditions in the eye. In one embodiment, the composition comprises from 10 ppm (or about 10 ppm) to 1000 ppm (or about 1000 ppm) of a polyquaternium having a weight average molecular weight of from about 150 to about 15,000 Daltons, from 0.001% (or about 0.001%) to 0.5% (or about 0.5%) of an anionic polymer having a weight average molecular weight of from about 250 Daltons to about 4,000,000 Daltons, and an effective amount of an organic acid, salts thereof or mixtures thereof, for binding with the polyquaternium in at least a 1:1 molar ratio, where, in certain embodiments, the composition is substantially free of cationic oligomer compounds and/or precipitation inhibiting compounds such as amphoteric surfactants having a weight average molecular weight of greater than about 303.4 Daltons.

The present invention further relates to a method of reducing, inhibiting or preventing the precipitation of a polyquaternium compound and an anionic polymer in a composition comprising such compounds, comprising the steps of:
i) providing from about 0.001% to about 0.5% of an anionic polymer having a weight average molecular weight of from about 250 to about 4,000,000 Daltons;
ii) adding an effective amount of an organic acid, salts thereof or mixtures thereof, such that the organic acid binds with the polyquaternium compound in at least a 1:1 molar ratio
iii) adding from about 10 ppm to about 1000 ppm of a polyquaternium compound having a weight average molecular weight of from about 150 to about 15,000 Daltons;

wherein the composition is substantially free of cationic oligomer compounds and precipitation inhibiting compounds.

DETAILED DESCRIPTION OF THE INVENTION

As indicated above, the present invention relates to ophthalmic compositions comprising an anionic polymer such as hyaluronic acid (HA) preserved with a polyquaternium compound such as polyquaternium-42 wherein precipitate formation or complexation of the anionic polymer and polyquaternium compound is reduced and/or prevented.

The compositions and methods of the present invention can comprise, consist of, or consist essentially of the steps, essential elements and limitations of the invention described herein, as well any of the additional or optional ingredients, components, or limitations described herein. The term "comprising" (and its grammatical variations) as used herein is used in the inclusive sense of "having" or "including" and not in the exclusive sense of "consisting only of." The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference are only incorporated herein to the extent that they are not inconsistent with this specification.

The term "effective amount" means that amount of the organic acid necessary to achieve complete association of the organic acid with the polyquaternium compound such that the molar ratio of the organic acid with the polyquaternium compound is at least 1:1.

The term "clear" means the absence of cloudiness and/or particles upon visual inspection.

As used herein, the term "visual inspection" means that a human viewer can visually discern the presence of particles or cloudiness with the unaided eye (excepting standard corrective lenses adapted to compensate for near-sightedness, farsightedness, or stigmatism, or other corrected vision) in lighting at least equal to the illumination of a standard 75 watt incandescent white light bulb at a distance of about 0.25 meter.

In certain embodiments, the present invention as disclosed herein may be practiced in the absence of any compound or element (or group of compounds or elements) which is not specifically disclosed herein.

Polyquaternium Compound

The compositions of the present invention comprise a polyquaternium compound. Polyquaternium is the International Nomenclature for Cosmetic Ingredients designation for several polycationic polymers that are used in the personal care industry. These polymers have quaternary ammonium centers in the polymer. INCI has approved at least 37 different polymers under the polyquaternium designation. They are cationic molecules. Some have antimicrobial properties, and find particular application in conditioners, shampoo, hair mousse, hair spray, hair dye, and contact lens solutions. Different polymers are distinguished by the numerical value that follows the word "polyquaternium". The numbers are assigned in the order in which they are registered rather than because of their chemical structure. Some of the more common quaternary ammonium compounds include those generically referred to in the art as polyquaternium.

In some embodiments, the composition will contain a polyquaternium having a weight average molecular weight of from about 150 to about 15,000 Daltons, optionally from about 200 to about 13,500 Daltons, or optionally from about 250 to about 12,000 Daltons in a level of from about 10 ppm to about 1000 ppm, or from about 12 ppm to about 200 ppm, or from about 15 ppm to about 65 ppm of a polyquaternium.

Examples of suitable polyquaternium compounds include, but are not limited to, polyquaternium-1, polyquaternium-10, polyquaternium-42 or mixtures. In an embodiment of the present invention, the polyquaternium compound is polyquaternium-42.

Polyquaternium-1 is also known as ethanol, 2,2',2"-nitrilotris-, polymer with 1,4-dichloro-2-butene and N,N,N',N'-tetramethyl-2-butene-1,4-diamine. Polyquaternium-10 is also known as quaternized hydroxyethyl cellulose. Polyquaternium-42 is also known as poly[oxyethylene(dimethylimino)ethylene (dimethylimino)ethylene dichloride].

Polyquaternium compounds are generally known to form precipitates with anionic polymers. In some instances, concentrations of the results in the precipitate formation and/or complexation with anionic polymers present in the composition.

Anionic Polymer

The compositions of the present invention comprise an anionic polymer having a weight average molecular weight of from about 250 to about 4,000,000, optionally from about 50,000 to about 3,000,000, optionally from about 75,000 to about 2,000,000, or optionally from about 100,000 to about 1,500,000 Daltons. Anionic polymers are polymers formed by anionic addition polymerization. Anionic addition polymerization is a form of chain-growth polymerization or addition polymerization that involves the polymerization of vinyl monomers with strong electronegative group. As noted above, these polymers would normally be dismissed as incompatible with cationic compounds (i.e. would form a precipitate in the combination with cationic compounds).

Examples of suitable anionic polymers, include, but are not limited to: sodium alginate (alginate), linear sulphated polysaccharides that are extracted from red edible seaweeds (carageenans), carbo-benzens (carbomers), high molecular weight, non-linear polyacrylic acid cross-linked with polyalkenyl polyethers sold under the trade name CARBOPOL (Lubrizol Advanced Materials, Inc. Cleveland, Ohio), sodium carboxymethylcellulose (sodium CMC), internally cross-linked sodium carboxymethylcelluloses (Croscarmellose sodium), water-soluble polysaccharides produced by *Pseudomonas elodea*, a bacterium also known as gellan gum (in certain embodiments the low acyl form of gellan gum is used) such as those sold under the trade name KELCOGEL (CP Kelco U.S., Inc., Atlanta, Ga.), anionic, nonsulfated glycosaminoglycans known as Hyaluronan (also called hyaluronic acid or hyaluronate or HA), structural heteropolysaccharides known as Pectin, polysaccharides secreted by the bacterium *Xanthomonas campestris* known as Xanthan Gum such as those sold under the trade name KELTROL (CP Kelco U.S., Inc., Atlanta, Ga.), maleic/alkylvinyl ether copolymers such as those sold under the trade name Gantrez (Ashland, N.J.) and mixtures of thereof.

In some embodiments, the composition will contain an anionic polymer in a level from about 0.001 to about 0.5%, or from about 0.005% to about 0.25%, or from about 0.01% to about 0.2% anionic polymer.

Hyaluronic acid is a linear polysaccharide (long-chain biological polymer) formed by repeating disaccharide units consisting of D-glucuronic acid and N-acetyl-D-glucosamine linked by $\beta(1-3)$ and $\beta(1-4)$ glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate discs, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

In certain embodiments, the maleic/alkylvinyl ether copolymer included in embodiments of the present invention may have a weight average molecular weight of between about 200,000 Daltons and about 1,500,000 Daltons, and/or a polydispersity index of between about 2 and 6. The maleic and alkylvinyl ether monomer segments may be randomly arranged in one embodiment. In another embodiment the monomer segments are alternating such that the resulting maleic/alkylvinyl ether copolymer has a structure similar to that illustrated by the following general maleic methylvinyl ether copolymer structure:

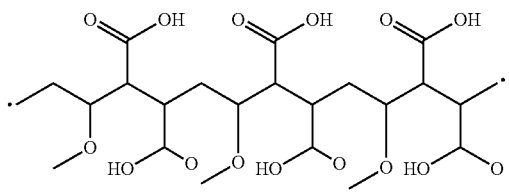

In certain embodiments, the compositions of the present invention comprise the free acid of methyl vinyl ether/maleic anhydride copolymer having a weight average molecular weight of between about 200,000 Daltons and about 1,500,000 Daltons, optionally from 200,000 Daltons to about 700,000 Daltons. In one embodiment, the free acid methyl vinyl ether/maleic anhydride copolymer is Gantrez® S-95 which has an average weight-average molecular weight of about 216,000 Daltons. In another embodiments, the free acid methyl vinyl ether/maleic anhydride copolymer is Gantrez® S-96 which has a weight-average molecular weight of about 700,000 Daltons.

Mixtures of maleic/alkylvinyl ether copolymers may also be employed. In one embodiment, a composition of the of the present invention may contain at least about 1% by weight (active amount) maleic/alkylvinyl ether copolymer, more particularly between about 1% and 15% by weight maleic/alkylvinyl ether copolymer, even more particularly, between about 1% and 10% by weight maleic/alkylvinyl ether copolymer.

In some embodiments, the anionic polymer is selected from the group consisting of hyaluronic acid (HA), gellan gum, methyl vinyl ether/maleic anhydride copolymer (optionally, the free acid thereof) or mixtures thereof.

Organic Acid

The compositions of the present invention comprise an organic acid, salts thereof (such the sodium or potassium salts of the organic acids) and mixtures of any of the preceding components. In certain embodiments, the organic acid has a solubility of at least 10 (or about 10) g/100 ml water at 25° C., optionally, at least 20 (or about 20) g/100 ml water at 25° C., optionally, at least 30 (or about 30) g/100 ml water at 25° C., optionally, at least 40 (or about 40) g/100 ml water at 25° C., optionally, at least 50 (or about 50) g/100 ml water at 25° C., or, optionally, at least 60 (or about 60) g/100 ml water at 25° C. and, optionally, no greater than 150 (or about 150) g/100 ml water at 25° C. Table 1 shows select list of organic acids and their solubility as cited in Merck Index, Twelfth Edition, Whitehouse Station, N.J. 1996.

TABLE 1

Solubility of Select Organic Acids

| Organic Acid | Solubility (g/100 ml water at 25° C.) |
|---|---|
| Formic acid | >100 |
| Acetic acid | 100 |
| Propionic acid | >100 |
| Oxalic acid | 8.34 |
| Succinic acid | 8 |
| Glutaric acid | 63.9 |
| Maleic acid | 78 |
| Fumaric acid | 0.63 |

TABLE 1-continued

Solubility of Select Organic Acids

| Organic Acid | Solubility (g/100 ml water at 25° C.) |
|---|---|
| Adipic acid | about 1 |
| L-Tartaric acid | >100 |
| Citric acid | 59.2 |
| Sodium Citrate, Dihydrate | about 77 |
| Ethylenediaminetetraacetic acid | 0.05 |

Suitable organic acids of the present invention include, but are not limited to, carboxylic acids, dicarboxylic acids, tricarboxylic acids, salts thereof, and mixtures thereof.

Examples of carboxylic acids include, but are not limited to, formic acid, acetic acid, propionic acid, salts thereof, and mixtures thereof.

Examples of dicarboxylic acids include, but are not limited to, glutaric (i.e. pentanedioic) acid, maleic acid, tartaric acid, salts thereof, and mixtures thereof.

Examples of tricarboxylic acids include, but are not limited to, citric acid, isocitric acid, salts thereof and mixtures thereof.

The tricarboxylic acid citric acid is a weak organic acid with the formula $C_6H_8O_7$. It is a natural preservative/conservative which occurs naturally in citrus fruits and is also used to add an acidic or sour taste to foods and drinks. In biochemistry, the conjugate base of citric acid, citrate, is important as an intermediate in the citric acid cycle, which occurs in the metabolism of all aerobic organisms. It consists of 3 carboxyl (R—COOH) groups.

In certain embodiments, the organic acid is selected from the group consisting of carboxylic acids, dicarboxylic acids, tricarboxylic acids, salts thereof and mixtures thereof. In one embodiment, the organic acid is citric acid. In another embodiment, the organic acid is tartaric acid.

In some embodiments, the composition will contain a molar ratio of organic acid to monomer unit of the polyquaternium compound of at least 1:1 (or about 1:1), optionally, at least 10:1 (or about 10:1), optionally, at least 100:1 (or about 100:1), optionally, at least 250:1 (or about 250:1), optionally, at least 350:1 (or about 350:1), or, optionally, at least 1000:1 (or about 1000:1). Optionally, the molar ratio of the organic acid to monomer unit of the polyquaternium compound is no greater than 5000:1 (or about 5000:1), or, optionally, no greater than 10,000:1 (or about 10,000:1).

In certain embodiments, a premix of the polyquaternium compound and the organic acid of the present invention or a premix of the anionic polymer and the organic acid of the present invention is formed prior to mixing of the polyquaternium compound and the anionic polymer.

The compositions of present invention are substantially free of cationic oligomer compounds and precipitation inhibiting compounds. The term "precipitation inhibiting compounds" means compounds, other than the organic acids of the present invention, which inhibit, reduce, or prevent the precipitation of the polyquaternium compounds and the anionic polymers. Examples of precipitation inhibiting compounds include, but are not limited to, amphoteric surfactants having a weight average molecular weight of greater than 303 (or about 303) Daltons. Amphoteric surfactants have the general formula I:

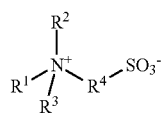 (I)

wherein $R^1$ is R or —$(CH_2)n$—NHC(O)R, wherein R is a $C_8$-$C_{30}$ alkyl optionally substituted with hydroxyl and n is 2, 3, or 4; $R^2$ and $R^3$ are each independently selected from the group consisting of hydrogen and $C_1$-$C_4$ alkyl; $R^4$ is a $C_2$-$C_8$ alkylene optionally substituted with hydroxyl; and $SO_3$— can also be further substituted by $CO_2$—. The invention would also exclude alkylamido betaines such as alkylamidopropyl betaines, cocoamidopropyl betaine, and lauroyl amidopropyl dimethyl betaine. Such amphoteric surfactants are useful in removing proteins and lipids and may, therefore, disrupt tear lipids in the eye which are essential to preventing evaporation of tear film. Accordingly, they are not desired for the compositions of this invention which are intended for instillation in the eye.

As noted above, the compositions of the present invention are also substantially free of cationic oligomers or nitrogen/amine oligomers having a number average molecular weight (MNO) from 500 Daltons to 15,000 Daltons (hereinafter referred to as cationic oligomer compounds), wherein the cationic oligomer or nitrogen/amine oligomer is present in the composition from 0.01 wt. % to 1.0 wt. %, and the composition comprises a ratio MNO:MNA from 5:1 to 1:5. Cationic oligomer compounds in contact lens solutions are intended to compete with cationic antimicrobial components to minimize adsorption of the cationic compound onto contact lenses. Without being limited by theory, it is believed, however, that such competition may compromise the activity of the polyquaternium compound in the compositions of the present invention.

The term "substantially free" as related to the cationic oligomer compounds and precipitation inhibiting compounds means that the oligomer compounds and/or the precipitation inhibiting compounds are present in the compositions of the present invention at a concentration of less than 5% (or about 5%), optionally less than 2.5% (or about 2.5%), and optionally less than 1% (or about 1%), optionally less than 0.1% (or about 0.1%), or optionally less than 0.01% (or about 0.01%). Optionally, the compositions of the present invention are free of cationic oligomer compounds and precipitation inhibiting compounds.

Optional Components

The compositions of the present invention may optionally comprise one or more additional excipients and/or one or more additional active ingredients. Excipients commonly used in ophthalmic compositions include, but are not limited to, demulcents, tonicity agents, preservatives, chelating agents, buffering agents (other than and in addition to the organic acids of the present invention), and surfactants. Other excipients comprise solubilizing agents, stabilizing agents, comfort-enhancing agents, polymers, emollients, pH-adjusting agents (other than and in addition to the organic acids of the present invention), and/or lubricants. Any of a variety of excipients may be used in the compositions of the present invention including water, mixtures of water and water-miscible solvents, such as vegetable oils or mineral oils comprising from 0.5% to 5% non-toxic water-soluble polymers, natural products, such as agar and acacia, starch derivatives, such as starch acetate and hydroxypropyl starch, and also other synthetic products such as polyvinyl alcohol, polyvinylpyrrolidone, polyvinyl methyl ether, polyethylene oxide, and preferably cross-linked polyacrylic acid and mixtures thereof.

Demulcents or soothing agents used with embodiments of the present invention include, but are not limited to, cellulose derivatives (such hydroxyethyl cellulose, methyl cellulose, hypromellose or mixtures thereof), glycerin, polyvinyl pyrrolidone, polyethylene oxide, polyethylene glycol, propylene glycol and polyacrylic acid. In certain embodiments, propylene glycol and polyethylene glycol 400 are the demulcents.

Suitable tonicity-adjusting agents include, but are not limited to, mannitol, sodium chloride, glycerin, and the like. Suitable buffering agents include, but are not limited to, phosphates, borates, acetates and the like, and amino alcohols such as 2-amino-2-methyl-1-propanol (AMP), salts of any of the above and mixtures of any of the above mentioned agents. Suitable surfactants include, but are not limited to, ionic and nonionic surfactants (though nonionic surfactants are preferred), RLM 100, POE 20 cetylstearyl ethers such as Procol® CS20, poloxamers such as Pluronic® F68, and block copolymers such as poly(oxyethylene)-poly(oxybutylene) compounds set forth in U.S. Patent Application Publication No. 2008/0138310 entitled "Use of PEO-PBO Block Copolymers in Ophthalmic Compositions" filed Dec. 10, 2007 (which publication is herein incorporated by reference).

Compositions of the present invention are ophthalmically suitable for application to a subject's eyes. The term "aqueous" typically denotes an aqueous formulation wherein the excipient is >about 50%, more preferably >about 75% and in particular >about 90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the composition as it is delivered, such devices being known in the art.

In certain embodiments, the compositions of the present invention are isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The compositions of the present invention generally have an osmolality in the range of 220-320 mOsm/kg, or, optionally, have an osmolality in the range of 235-300 mOsm/kg. The ophthalmic compositions will generally be formulated as sterile aqueous solutions.

The compositions of the present invention can also be used to administer pharmaceutically active compounds. Such compounds include, but are not limited to, glaucoma therapeutics, pain relievers, anti-inflammatory and anti-allergy medications, and anti-microbials. More specific examples of pharmaceutically active compounds include betaxolol, timolol, pilocarpine, carbonic anhydrase inhibitors and prostglandins; dopaminergic antagonists; post-surgical antihypertensive agents, such as para-amino clonidine (apraclonidine); anti-infectives such as ciprofloxacin, moxifloxacin, and tobramycin; non-steroidal and steroidal anti-inflammatories, such as naproxen, diclofenac, nepafenac, suprofen, ketorolac, tetrahydrocortisol and dexamethasone; dry eye therapeutics such as PDE4 inhibitors; and anti-allergy medications such as H1/H4 inhibitors, H4 inhibitors, olopatadine or mixtures thereof.

It is also contemplated that the concentrations of the ingredients comprising the formulations of the present invention can vary. A person of ordinary skill in the art would understand that the concentrations can vary depending on the addition, substitution, and/or subtraction of ingredients in a given formulation.

In certain embodiments, the compositions of the present invention are buffered, using buffering agents, such that the compositions maintain a pH of from about 5.0 to a pH of about 8.0, optionally a pH of from about 6.5 to a pH of about 8.0. Topical formulations (particularly topical ophthalmic formulations, as noted above) are preferred which have a physiological pH matching the tissue to which the formulation will be applied or dispensed.

In certain embodiments, the compositions of the present invention is in the form of eye-drop solution, eye wash solution, contact lens lubricating and/or rewetting solution, spray, mist or any other manner of administering a composition to the eye.

In particular embodiments, the composition of the present invention are formulated for administration at any frequency of administration, including once a week, once every five days, once every three days, once every two days, twice a day, three times a day, four times a day, five times a day, six times a day, eight times a day, every hour, or greater frequency. Such dosing frequency is also maintained for a varying duration of time depending on the therapeutic needs of the user. The duration of a particular therapeutic regimen may vary from one-time dosing to a regimen that extends for months or years. One of ordinary skill in the art would be familiar with determining a therapeutic regimen for a specific indication.

EXAMPLES

The compositions of the present invention as described in following examples illustrate specific embodiments of compositions of the present invention, but are not intended to be limiting thereof. Other modifications can be undertaken by the skilled artisan without departing from the spirit and scope of this invention.

Example 1: Solution with Anionic Polymer and Polyquaternium Compound

A solution was prepared containing both an anionic polymer (Gellan Gum) and a Polyquaternium compound (PQ42). Table 2 shows the list of ingredients.

TABLE 2

Example 1 components.

| INGREDIENT | % w/w | amount per batch (gms) |
|---|---|---|
| Hypromellose | 0.200 | 0.150 |
| Gellan Gum | 0.020 | 0.015 |
| Polyquaternium 42 | 0.003 | 0.00225 |
| Sodium Citrate, Dihydrate | 1.755 | 1.316 |
| Purified Water | 98.022 | 73.5165 |
| total | 100.00% | 75.00 g |

The hypromellose was Methocel E4M Premium, supplied by DOW CHEMICAL (MIDLAND, Mich.). The gellan gum was Kelcogel CG-LA low acyl, supplied by CP KELCO (ATLANTA, Ga.). The Polyquaternium 42 was supplied as Polyquaternium 42 (33% aqueous) by DSM BIOMEDICAL (BERKELEY, Calif.). The sodium citrate, dihydrate was tri-Sodium Citrate Dihydrate Powder supplied by MERCK (DARMSTADT, GERMANY).

The procedure for preparing the solution was as follows:
1. The 1.316 grams of Sodium Citrate Dihydrate was added to 45 grams of Purified Water USP in a container. The solution was mixed until the Sodium Citrate Dihydrate dissolved.
2. To the above was added 0.225 grams of a 1% solution of Polyquaternium 42 in water. The solution was mixed until the Polyquaternium 42 dissolved.
3. An additional 3.46 grams of water was added and mixed until the solution was uniform.
4. In a separate a container, a 1 liter solution of 0.06% Gellan Gum and 0.60% Hypromellose was prepared by adding 0.60 grams of Gellan Gum slowly to 950 g of water heated to a temperature greater than 40° C. The temperature of the solution was increased to 75° C. while mixing. When a temperature of 75° C. was achieved, the solution was mixed for 15 minutes, while maintaining a constant temperature of 75° C. The temperature of the solution was then increased to 80° C. to 85° C. To this solution, 6 grams of Hypromellose was then slowly added. When addition of Hypromellose was completed, the temperature was kept constant from 80° C. to 85° C. for 15 minutes. The solution was mixed until ambient temperature, q.s.ed with water, and mixed an additional 15 minutes.
5. To the solution of Step 3 was slowly added 25 grams of the 0.06% Gellan Gum and 0.60% Hypromellose solution of Step 4.

On completion of addition of all ingredients, it was noted that the solution containing the sodium citrate as the organic acid was clear regardless of the solution containing both Gellan Gum and Polyquaternium 42. The sodium citrate, dihydrate used in this example had a solubility from Table 1 of about 77 g/100 ml of water (at 25° C.)—or a solubility greater than the 10 g/100 ml threshold solubility (at 25° C.) for organic acids useful in the present invention.

Example 2: Solutions with Anionic Polymer and Polyquaternium Compound

A solution was prepared containing both an anionic polymer (Gellan Gum) and a Polyquaternium compound (PQ42). Table 3 shows the list of ingredients.

TABLE 3

Example 2 components.

| | 2A | | 2B | |
|---|---|---|---|---|
| INGREDIENT | % w/w | amount per batch (gms) | % w/w | amount per batch (gms) |
| Hypromellose | 0.200 | 0.150 | 0.200 | 0.150 |
| Gellan Gum | 0.020 | 0.015 | 0.020 | 0.015 |
| Polyquaternium 42 | 0.003 | 0.00225 | 0.003 | 0.00225 |
| Sodium Citrate, Dihydrate | 0.1368 | 0.1026 | 1.368 | 1.026 |
| Purified Water | 99.6402 | 74.73015 | 98.409 | 73.80675 |
| total | 100.00% | 75.00 g | 100.00% | 75.00 g |

The hypromellose was Methocel E4M Premium, supplied by DOW CHEMICAL (MIDLAND, Mich.). The gellan gum was Kelcogel CG-LA low acyl, supplied by CP KELCO (ATLANTA, Ga.). The Polyquaternium 42 was supplied as Polyquaternium 42 (33% aqueous) by DSM BIOMEDICAL (BERKELEY, Calif.). The sodium citrate, dihydrate was tri-Sodium Citrate Dihydrate Powder, supplied by MERCK (DARMSTADT, GERMANY).

The procedure for preparing the solutions was as follows:
1. The Sodium Citrate Dihydrate was added to 45 grams of Purified Water USP. The solution was mixed until the Sodium Citrate Dihydrate dissolved.
2. To the above was added 0.225 grams of a 1% solution of Polyquaternium 42 in water. The solution was mixed until the Polyquaternium 42 dissolved.
3. The additional of water was added and mixed until the solution was uniform.
4. Slowly added to the solution of Step 3 was 25 grams of a 0.06% Gellan Gum and 0.60% Hypromellose solution as prepared in Step 4 of Example 1.

On completion of addition of all ingredients, it was noted that Solution 2A having a molar ratio of sodium citrate to monomer unit of Polyquaternium 42 of about 40:1 was slightly cloudy yet uniform, indicating that insufficient Citrate was available to prevent incompatibility of Gellan Gum and Polyquaternium 42. Solution 2B having a molar ratio of sodium citrate to monomer unit of Polyquaternium 42 of about 400:1 was clear regardless of the solution containing both Gellan Gum and Polyquaternium 42. The sodium citrate, dihydrate used in this example had a solubility from Table 1 of about 77 g/100 ml of water (at 25° C.)—or a solubility greater than the 10 g/100 ml threshold solubility (at 25° C.) for organic acids useful in the present invention. This example shows that there is a finite ratio of citrate to cationic polyquaternium needed to overcome incompatibility with anionic polymer.

Example 3: Solutions with Anionic Polymer and Polyquaternium Compound

A solution was prepared containing both and anionic polymer (Sodium Hyaluronate) and a Polyquaternium compound (PQ42). Table 4 shows the list of ingredients.

TABLE 4

| | Example 3 components. | | | | | |
|---|---|---|---|---|---|---|
| | 3A | | 3B | | 3C | |
| INGREDIENT | % w/w | amount per batch (gms) | % w/w | amount per batch (gms) | % w/w | amount per batch (gms) |
| Sodium Hyaluronate | 0.200 | 0.100 | 0.200 | 0.100 | 0.200 | 0.100 |
| Polyquaternium 42 | 0.003 | 0.0015 | 0.003 | 0.0015 | 0.003 | 0.0015 |
| Sodium Citrate, Dihydrate | — | — | 2.000 | 1.000 | 2.000 | 1.000 |
| Citric Acid, anhydrous | — | — | 0.100 | 0.050 | 0.100 | 0.050 |
| Purified Water | 99.797 | 49.8985 | 97.697 | 48.8485 | 97.697 | 48.8485 |
| total | 100.00% | 50.00 g | 100.00% | 50.00 g | 100.00% | 50.00 g |

The sodium hyaluronate was supplied by LIFECORE (CHASKA, Minn.). The Polyquaternium 42 was supplied as Polyquaternium 42 (33% aqueous) by DSM BIOMEDICAL (BERKELEY, Calif.). The sodium citrate, dihydrate was tri-Sodium Citrate Dihydrate Powder supplied by MERCK (DARMSTADT, GERMANY). The citric acid anhydrous was supplied by VWR/BDH (WEST CHESTER, Pa.).

The procedure for preparing the Solution 3A was as follows:
1. Into a beaker was poured 16.67 grams of a 0.6% Sodium Hyaluronate Solution which was prepared by adding 150 grams of water into a separate container and slowly adding 1 gram of Sodium Hyaluronate into the water. The solution was mixed for 2 hours at ambient temperature to disperse the Sodium Hyaluronate. Additional water was added to bring the total amount of the solution to 166 grams and mixing the solution an additional 10 minutes.
2. Next, 32.33 grams of Purified Water USP was added to the beaker while mixing to disperse and solubilize.
3. One gram of a solution of 0.015 grams of Polyquaternium 42 in 10 grams of Purified Water US was added to the above while mixing.

The procedure for preparing the Solution 3B was as follows:
1. Into a beaker was poured 16.67 grams of a 0.6% Sodium Hyaluronate Solution as prepared in Step 1 of the preparation of Solution 3A.
2. Next, 22.28 grams of Purified Water USP was added to the first beaker while mixing to disperse and solubilize.
3. Into a second beaker, 8.9485 grams of Purified Water USP was poured.
4. Next, 0.015 grams of Polyquaternium 42 was added to the second beaker while mixing.
5. One gram of Sodium Citrate Dihydrate and 0.050 grams of Citric Acid were added to the second beaker while mixing to disperse with Polyquaternium 42 premix.
6. The solution in the second beaker was added to the solution in the first beaker while mixing.

The procedure for preparing the Solution 3C was as follows:
1. Into a beaker was poured 16.67 grams of a 0.6% Sodium Hyaluronate Solution as prepared in Step 1 of the preparation of Solution 3A.
2. Next, 23.28 grams of Purified Water USP was added to the beaker while mixing to disperse and solubilize.
3. One gram of Sodium Citrate Dihydrate was added to the beaker while mixing.
4. Next, 0.050 grams of Citric Acid were added to the beaker while mixing.
5. Finally, 0.0045 grams of a solution of 33% Polyquaternium 42 was added to the beaker while mixing.

Solution 3A was extremely cloudy with evidence of a local precipitate indicative of incompatibility of Sodium Hyaluronate with Polyquaternium 42. Solutions 3B and 3C containing the sodium citrate, dihydrate/citric acid combination as the organic acid were clear regardless of the fact that the anionic polymer Sodium Hyaluronate was combined with Polyquaternium 42. The sodium citrate, dihydrate and citric acid used in this example had a solubilities from Table 1 of about 77 g and 59.2 g/100 ml of water (at 25° C.), respectively—or solubilities greater than the 10 g/100 ml threshold solubility (at 25° C.) for organic acids useful in the present invention.

It is important to note that in Solutions 3B and 3C that the citrate was added and dissolved first with Polyquaternium 42 prior to combining with the anionic polymer or added and dissolved first with anionic polymer before combining with Polyquaternium 42.

Example 4: Solutions with Anionic Polymer and Polyquaternium Compound

A solution was prepared containing both and anionic polymer (Gellan Gum) and a Polyquaternium compound (PQ42). Table 5 shows the list of ingredients.

TABLE 5

Example 4 components.

| INGREDIENT | 4A % w/w | 4A amount per batch (gms) | 4B % w/w | 4B amount per batch (gms) | 4C % w/w | 4C amount per batch (gms) |
|---|---|---|---|---|---|---|
| Hypromellose | 0.200 | 0.100 | 0.200 | 1.000 | 0.200 | 1.000 |
| Gellan Gum | 0.020 | 0.010 | 0.020 | 0.100 | 0.020 | 0.100 |
| Polyethylene Glycol 400 | — | — | — | — | 1.129 | 5.645 |
| Glycerin | — | — | — | — | 0.2527 | 1.264 |
| Sodium Citrate, Dihydrate | 2.000 | 1.000 | 2.000 | 10.000 | 2.000 | 10.000 |
| Citric Acid | 0.10 | 0.05 | 0.100 | 0.500 | 0.010 | 0.050 |
| Polyquaternium 42 | 0.003 | 0.0015 | 0.003 | 0.0015 | 0.003 | 0.015 |
| Edetate Disodium | — | — | 0.100 | 0.5 | 0.10 | 0.500 |
| Purified Water | 97.677 | 48.8385 | 97.577 | 487.885 | 96.2853 | 481.426 |
| total | 100.00% | 50.00 g | 100.00% | 500.00 g | 100.00% | 500.00 g |

The hypromellose was Methocel E4M Premium, supplied by DOW CHEMICAL (MIDLAND, Mich.). The gellan gum was Kelcogel CG-LA low acyl, supplied by CP KELCO (ATLANTA, Ga.). The Polyethylene Glycol 400 was Polyglykol 400 supplied by CLAMANT PRODUKTE (BURGKIRCHEN, GERMANY). The Glycerin was Edenor G 99.8 supplied by EMERY OLEOCHEMICALS (DUSSELDORF, GERMANY). The Polyquaternium 42 was supplied as Polyquaternium 42 (33% aqueous) by DSM BIOMEDICAL (BERKELEY, Calif.). The sodium citrate, dihydrate was tri-Sodium Citrate Dihydrate Powder supplied by MERCK (DARMSTADT, GERMANY). The citric acid anhydrous was supplied by VWR/BDH (WEST CHESTER, Pa.). The edetate disodium was Titriplex III supplied by MERCK (MOLLET DEL VALLES, SPAIN).

The procedure for preparing the Solution 4A was as follows:
1. 16.67 grams of a 0.6% Gellan Gum and 0.06% Hypromellose solution as prepared in Step 4 of Example 1 was added to a beaker.
2. 32.2655 grams of Purified Water USP was added to the beaker while mixing to disperse and dissolve the gellan gum and hypromellose.
3. Sequentially added the Sodium Citrate Dihydrate and Citric acid allowing time for the prior to dissolve before adding the latter.
4. 0.0045 grams of a solution of 33% Polyquaternium 42 was added to the beaker while mixing.

The procedure for preparing the Solution 4B was as follows:
1. Into a beaker was poured 166.7 grams of a 0.6% Gellan Gum and 0.06% Hypromellose solution as prepared in Step 4 of Example 1.
2. Next, 322.255 grams of Purified Water USP was added to the beaker while mixing to disperse and dissolve the gellan gum and hypromellose.
3. Sequentially added the 10 grams of Sodium Citrate Dihydrate and 0.5 grams of Citric acid allowing time for the prior to dissolve before adding the latter.
4. While mixing, 0.045 grams of a solution of 33% Polyquaternium 42 was added to the beaker.
5. Added 0.5 grams of Edetate Disodium and mixed the batch until dissolved.

The procedure for preparing the Solution 4C was as follows:
1. Into a beaker was poured 166.7 grams of a 0.6% Gellan Gum and 0.06% Hypromellose solution as prepared in Step 4 of Example 1.
2. Next, 315.346 grams of Purified Water USP was added to the beaker while mixing to disperse and dissolve the gellan gum and hypromellose.
3. Sequentially added 5.645 g of Polyethylene Glycol 400 and 1.264 g of Glycerin, allowing time for each to dissolve before proceeding.
4. Sequentially added the 10 grams of Sodium Citrate Dihydrate and 0.5 grams of Citric acid allowing time for the prior to dissolve before adding the latter.
5. While mixing, 0.045 grams of a solution of 33% Polyquaternium 42 was added to the beaker.
6. Added 0.5 grams of Edetate Disodium and mixed the batch until dissolved.

All three solutions containing the sodium citrate, dihydrate/citric acid combination as the organic acid were clear. The sodium citrate, dihydrate and citric acid used in this example had solubilities from Table 1 of about 77 g and 59.2 g/100 ml of water (at 25° C.), respectively—or solubilities greater than the 10 g/100 ml threshold solubility (at 25° C.) for organic acids useful in the present invention. The tonicity of Solutions 4A and 4C were measured using a calibrated Advanced Instruments Osmometer (model 3320) supplied by Advanced Instruments (Norwood, Mass.). The tonicity of Solution 4A was 215 mOsm/Kg. This is suitable for a hypotonic ophthalmic solution. The tonicity of Solution 4C was 292 mOsm/Kg. This is suitable for a isotonic ophthalmic solution.

Example 5: Solutions with Anionic Polymer and Polyquaternium

A solution was prepared containing both and anionic polymer (Gellan Gum) and a Polyquaternium (PQ42). Table 6 shows the list of ingredients.

TABLE 6

Example 5 components.

| INGREDIENT | 5A % w/w | 5A amount per batch (gms) | 5B % w/w | 5B amount per batch (gms) |
|---|---|---|---|---|
| Hypromellose | 0.200 | 1.000 | 0.200 | 1.000 |
| Gellan Gum | 0.020 | 0.100 | 0.020 | 0.100 |
| Polyethylene Glycol 400 | 1.129 | 5.645 | 1.129 | 5.645 |
| Glycerin | 0.2527 | 1.264 | 0.2527 | 1.264 |
| Sodium Citrate, Dihydrate | 1.400 | 7.000 | 1.600 | 8.000 |
| Boric Acid | 0.500 | 2.500 | 0.580 | 2.900 |
| Polyquaternium 42 | 0.003 | 0.015 | 0.003 | 0.015 |
| Edetate Disodium | 0.10 | 0.500 | 0.10 | 0.500 |
| Purified Water | 96.3953 | 481.976 | 96.1153 | 480.576 |
| total | 100.00% | 500.00 g | 100.00% | 500.00 g |

The hypromellose was Methocel E4M Premium, supplied by DOW CHEMICAL (MIDLAND, Mich.). The gellan gum was Kelcogel CG-LA low acyl, supplied by CP KELCO (ATLANTA, Ga.). The Polyethylene Glycol 400 was Polyglykol 400 supplied by CLAMANT PRODUKTE (BURGKIRCHEN, GERMANY). The Glycerin was Edenor G 99.8 supplied by EMERY OLEOCHEMICALS (DUSSELDORF, GERMANY). The Boric acid was supplied by MERCK (DARMSTADT, GERMANY). The Polyquaternium 42 was supplied as Polyquaternium 42 (33% aqueous) by DSM BIOMEDICAL (BERKELEY, Calif.). The sodium citrate, dihydrate was tri-Sodium Citrate Dihydrate Powder, supplied by MERCK (DARMSTADT, GERMANY). The citric acid anhydrous was supplied by VWR/BDH (WEST CHESTER, Pa.). The edetate disodium was Titriplex III supplied by MERCK (MOLLET DEL VALLES, SPAIN).

The procedure for preparing the Solution 5A was as follows:
1. Into a beaker was poured 166.7 grams of a 0.6% Gellan Gum and 0.06% Hypromellose solution as prepared in Step 4 of Example 1.
2. Next, 308.3 grams of Purified Water USP was added to the beaker while mixing to disperse and dissolve the gellan gum and hypromellose.
3. Sequentially added 5.645 g of Polyethylene Glycol 400 and 1.264 g of Glycerin, allowing time for each to dissolve before proceeding.
4. Next, added the 4 grams of Sodium Citrate Dihydrate and mix until dissolved.
5. While mixing, 0.045 grams of a solution of 33% Polyquaternium 42 was added to the beaker.
6. Added 0.5 grams of Disodium Edetate and mixed the batch until dissolved.
7. The following ingredients are added in sequence and dissolved to adjust pH of the final solution:
1.6 gm Boric acid, 2 gm Sodium Citrate Dihydrate, 0.5 gm Boric acid, 1 gm Sodium Citrate Dihydrate, and 0.4 gm Boric acid.

The procedure for preparing the Solution 5B was as follows:
1. Into a beaker was poured 166.7 grams of a 0.6% Gellan Gum and 0.06% Hypromellose solution as prepared in Step 4 of Example 1.
2. Next, 308.3 grams of Purified Water USP was added to the beaker while mixing to disperse and dissolve the gellan gum and hypromellose.
3. Sequentially added 5.645 g of Polyethylene Glycol 400 and 1.264 g of Glycerin, allowing time for each to dissolve before proceeding.
4. Next, added the 8 grams of Sodium Citrate Dihydrate and mix until dissolved.
5. While mixing, 0.045 grams of a solution of 33% Polyquaternium 42 was added to the beaker.
6. Added 0.5 grams of Disodium Edetate and mixed the batch until dissolved.
7. Added 2.9 grams of Boric acid and mixed the batch until dissolved.
8. Sufficient water was added to bring the batch total to 500 grams.

Both solutions containing the sodium citrate, dihydrate as the organic acid were clear. The sodium citrate, dihydrate used as the organic acid in this example had a solubility from Table 1 of about 77 g/100 ml of water (at 25° C.)—or a solubility greater than the 10 g/100 ml threshold solubility (at 25° C.) for organic acids useful in the present invention. The tonicity of Solution 5A was measured as discussed in Example 4 above. The tonicity of Solution 5A was 290 mOsm/Kg. This is suitable for an isotonic ophthalmic solution. The pH of Solution 5A was 6.8, within the pH of natural tears. The pH of Solution 5B was 7.0.

Example 6: Solutions with Anionic Polymer and Polyquaternium

A solution was prepared containing both and anionic polymer (Sodium Hyaluronate) and a Polyquaternium (PQ42). Table 7 shows the list of ingredients.

TABLE 7

Example 6 components.

| | 6A | | 6B | |
|---|---|---|---|---|
| INGREDIENT | % w/w | amount per batch (gms) | % w/w | amount per batch (gms) |
| Sodium Hyaluronate | 0.200 | 0.200 | 0.200 | 0.200 |
| Polyquaternium 42 | 0.005 | 0.005 | 0.005 | 0.005 |
| Sodium Citrate, Dihydrate | 0.350 | 0.350 | 0.350 | 0.350 |
| Citric Acid, anhydrous | 0.009 | 0.009 | — | — |
| Purified Water | 99.436 | 99.436 | 99.445 | 99.445 |
| 1N Sodium Hydroxide | * | * | — | — |
| 1N Hydrochloric Acid | * | * | — | — |
| total | 100.00% | 100.000 | 0.10 | 0.500 |

*To adjust pH

The Sodium Hyaluronate was supplied by LIFECORE (CHASKA, Minn.). The Polyquaternium 42 was supplied as Polyquaternium 42 (33% aqueous) by DSM BIOMEDICAL (BERKELEY, Calif.). The sodium citrate, dihydrate was tri-Sodium Citrate Dihydrate Powder supplied by MERCK (DARMSTADT, GERMANY). The citric acid anhydrous was supplied by VWR/BDH (WEST CHESTER, Pa.).

The procedure for preparing the Solution 6A was as follows:
1. Into a beaker was poured 99 grams of a solution of 0.2% Sodium Hyaluronate which was prepared by adding 988 grams of water into a separate container and slowly adding 2 gram of Sodium Hyaluronate into the water. The solution was mixed for 2 hours at ambient temperature to disperse the Sodium Hyaluronate. Additional water was added to bring the total amount of the solution to 990 grams and mixing the solution an additional 10 minutes.
2. Next, 0.009 grams of Citric Acid was added to the beaker while mixing.
3. The pH was adjusted to 7.35 using 1N Sodium Hydroxide or 1N Hydrochloric Acid.
4. While mixing, 0.015 grams of a solution of 33% Polyquaternium 42 was added to the beaker.
5. Finally, 0.35 grams of Sodium Citrate Dihydrate was added and mix until dissolved.

The procedure for preparing the Solution 6B was as follows:
1. Into a beaker was poured 99 grams of a 0.2% Sodium Hyaluronate solution as prepared in Step 1 of the preparation of Solution 6A.
2. Next, 0.35 grams of Sodium Citrate Dihydrate was added and mix until dissolved.
3. The pH was measured to be 7.6.
4. While mixing, 0.015 grams of a solution of 33% Polyquaternium 42 was added to the beaker.

Both solutions containing the sodium citrate, dihyate or the sodium citrate, dihydrate/citric acid combination, in each case, as the organic acid were clear. The sodium citrate, dihydrate and citric acid used in this example had solubilities from Table 1 of about 77 g and 59.2 g/100 ml of water (at 25° C.), respectively—or solubilities greater than the 10 g/100 ml threshold solubility (at 25° C.) for organic acids useful in the present invention.

Example 7: Solution with Anionic Polymer and Polyquaternium

A solution was prepared containing both and anionic polymer (Sodium Hyaluronate) and a Polyquaternium (PQ42). Table 8 shows the list of ingredients.

TABLE 8

Example 7 components.

| INGREDIENT | % w/w | amount per batch (gms) |
|---|---|---|
| Sodium Hyaluronate | 0.200 | 0.200 |
| Polyquaternium 42 | 0.005 | 0.005 |
| L-Tartaric Acid | 5.0 | 5.0 |
| Purified Water | 94.785 | 94.785 |
| total | 100.00% | 100.000 |

The Sodium Hyaluronate was supplied by LIFECORE (CHASKA, Minn.). The Polyquaternium 42 was supplied as Polyquaternium 42 (33% aqueous) by DSM BIOMEDICAL (BERKELEY, Calif.). The L-Tartaric Acid was supplied by AMRESCO (SOLON, Ohio).

The procedure for preparing the Solution 7 was as follows:

1. Into a beaker was poured 50 grams of a 0.4% Sodium Hyaluronate solution which was prepared by adding 2958 grams of water into a separate container and slowly adding 12 grams of Sodium Hyaluronate into the water. The solution was mixed for 3 hours at ambient temperature to disperse the Sodium Hyaluronate. Additional water was added to bring the total amount of the solution to 3000 grams and mixing the solution an additional 10 minutes.
2. To the above 50 grams of 0.4% Sodium Hyaluronate solution was added 44 grams of water and the solution was mixed for 5 minutes to disperse the polymer uniformly.
3. While continuing to mix, 5 grams of L-Tartaric acid was added to the above solution. The solution was mixed an additional 5 minutes.
4. The above quantity of Polyquaternium 42, supplied as: 0.0015 grams of 33% Polyquaternium 42 was next added to the solution.
5. The solution was q.s.ed to 100 grams and mixed an additional 5 minutes.

The solution containing the L-tartaric acid as the organic acid was clear throughout the addition of the Polyquaternium 42 and remained clear. The L-tartaric acid used in this example had a solubility from Table 1 of >100 g/100 ml of water (at 25° C.)—or a solubility greater than the 10 g/100 ml threshold solubility (at 25° C.) for organic acids useful in the present invention.

Example 8: Solution with Anionic Polymer and Polyquaternium

A solution was prepared containing both and anionic polymer (Sodium Hyaluronate) and a Polyquaternium (PQ42). Table 9 shows the list of ingredients.

TABLE 9

Example 8 components.

| INGREDIENT | % w/w | amount per batch (gms) |
|---|---|---|
| Gantrez S-95 | 0.500 | 0.250 |
| Polyquaternium 42 | 0.003 | 0.0015 |
| Sodium Citrate, Dihydrate | 0.70 | 0.35 |
| Purified Water | 98.797 | 49.3985 |
| total | 100.00% | 50.000 |

The Gantrez S-95 was supplied by ASHLAND (WILMINGTON, Del.). The Polyquaternium 42 was supplied as Polyquaternium 42 (33% aqueous) by DSM BIOMEDICAL, (BERKELEY, Calif.). The sodium citrate, dihydrate was tri-Sodium Citrate supplied by MERCK (DARMSTADT, GERMANY).

The procedure for preparing the Solution 8 was as follows:

1. Into a beaker was poured 48.93 grams of Purified Water USP.
2. To the above was added 0.715 grams of Gantrez S-95 supplied as 35% aqueous solution while mixing to disperse.
3. To the above was added 0.0045 grams of Polyquaternium 42 (33% aqueous).
4. To the above cloudy dispersion was added 0.35 grams of Sodium Citrate Dihydrate while mixing.

The solution was cloudy prior to the addition of the Sodium Citrate, Dihydrate. Upon addition of the Sodium Citrate Dihydrate, the solution became clear. The sodium citrate, dehydrate used in this example as the organic acid had a solubility from Table 1 of about 77 g/100 ml of water (at 25° C.)—or a solubility greater than the 10 g/100 ml threshold solubility (at 25° C.) for organic acids useful in the present invention.

Example 9: Solution with Anionic Polymer and Polyquaternium

Solutions were prepared containing both and anionic polymer (Sodium Hyaluronate or Gantrez S-96) and a Polyquaternium (PQ42 or PQ10). Table 10 shows the list of ingredients for solutions 9A-9D.

TABLE 10

Example 9 components.

| INGREDIENT | 9A % w/w | 9A amount per batch (gms) | 9B % w/w | 9B amount per batch (gms) | 9C % w/w | 9C amount per batch (gms) | 9D % w/w | 9D amount per batch (gms) |
|---|---|---|---|---|---|---|---|---|
| Sodium Hyaluronate | 0.2 | 0.2 | — | — | 0.2 | 0.2 | — | — |
| Gantrez S-96 | — | — | 0.5 | 0.5 | — | — | 0.5 | 0.5 |
| Polyquaternium 10 | — | — | — | — | 0.1 | 0.1 | 0.1 | 0.1 |
| Polyquaternium 42 | 0.005 | 0.005 | 0.005 | 0.005 | — | — | — | — |
| Maleic Acid | 38.0 | 38.0 | 38.0 | 38.0 | 38.0 | 38.0 | 38.0 | 38.0 |
| Purified Water | 61.795 | 61.795 | 61.495 | 61.495 | 61.7 | 61.7 | 61.4 | 61.4 |
| total | 100.00% | 100.00 g | 100.00% | 100.00 g | 100.00% | 100.00 g | 100.00% | 100.00 g |

The sodium hyaluronate was supplied by LIFECORE (CHASKA, Minn.). The Gantrez S-96 was supplied by ASHLAND (WILMINGTON, Del.). Polyquaternium 42 was supplied as Polyquaternium 42 (33% aqueous) by DSM BIOMEDICAL, (BERKELEY, Calif.). Polyquaternium 10 was supplied by ALDRICH CHEMICALS (ST. LOUIS, Mo.). The maleic acid was supplied by ALFA AESAR (HEYSHAM, ENGLAND).

The procedure for preparing Solutions 9A and 9C was as follows:

1. Into a beaker was poured 100.00 grams of a 0.4% Sodium Hyaluronate Solution which was prepared by adding 2988 grams of water into a separate container and slowly adding 12 gram of Sodium Hyaluronate into the water. The solution was mixed for 2 hours at ambient temperature to disperse the Sodium Hyaluronate. Additional water was added to bring the total amount of the solution to 166 grams and mixing the solution an additional 10 minutes.
2. Next, 20 grams of Purified Water USP was added to the beaker while mixing to disperse and solubilize.
3. Next, 76 grams of Maleic acid was added and mixed. The temperature of the resulting cold undissolved mixture was 11.9° C. and the solution was heated to 25° C. to thoroughly dissolve the acid.
4. Half of the above solution was separated for use as described in step. 7.
5. A total of 0.015 gram of Polyquaternium 42 was added to the remaining half of solution of step 4 while mixing.
6. The solution was brought to 100 g using purified water and mixed for 5 minutes.
7. To the separated solution from step 4 was added 0.10 gram of Polyquaternium 10 while mixing.
8. The solution prepared in step 7 was brought to 100 g using purified water and mixed for 10 minutes.

The procedure for preparing Solutions 9B and 9D was as follows:

1. Into a beaker containing 110.00 grams of water was slowly added 7.7 gram of a 13% solution of Gantrez S-96 as supplied.
2. The solution was mixed for 5 minutes to uniformly dissolve the Gantrez S-96.
3. To the above was added 76.0 grams of Maleic acid resulting in a cold undissolved mixture at a temperature of 10.7° C.
4. The solution was heated to 25° C. and mixed to dissolve.
5. Half of the above solution was separated for use as described in step 8.
6. To the remaining solution in step 5 was added 0.015 gram of Polyquaternium 42 while mixing.
7. The solution was brought to 100 g using purified water and mixed for 10 minutes.
8. To the separated solution from step 5 was added 0.10 gram of Polyquaternium 10 while mixing.
9. The solution in step 8 was brought to 100 g using purified water and mixed for 10 minutes.

Solutions 9A, 9B, 9C, and 9D containing maleic acid as the organic acid were clear and colorless with no precipitation evident. The maleic acid used in this example had a solubility from Table 1 of 78 g/100 ml of water (at 25° C.)—or a solubility greater than the 10 g/100 ml threshold solubility (at 25° C.) for organic acids useful in the present invention.

Example 10: Solution with Anionic Polymer and Polyquaternium

Solutions were prepared containing both and anionic polymer (Sodium Hyaluronate or Gantrez S-96) and a Polyquaternium (PQ42 or PQ10). Table 11 shows the list of ingredients for solutions 10A-10D.

TABLE 11

Example 10 components.

| INGREDIENT | 10A % w/w | 10A amount per batch (gms) | 10B % w/w | 10B amount per batch (gms) | 10C % w/w | 10C amount per batch (gms) | 10D % w/w | 10D amount per batch (gms) |
|---|---|---|---|---|---|---|---|---|
| Sodium Hyaluronate | 0.2 | 0.2 | — | — | 0.2 | 0.2 | — | — |
| Gantrez S-96 | — | — | 0.5 | 0.5 | — | — | 0.5 | 0.5 |
| Polyquaternium 10 | — | — | — | — | 0.01 | 0.01 | 0.01 | 0.01 |
| Polyquaternium 42 | 0.005 | 0.005 | 0.005 | 0.005 | — | — | — | — |
| L-Tartaric Acid | 5.0 | 5.0 | 5.0 | 5.0 | 5.0 | 5.0 | 5.0 | 5.0 |
| Purified Water | 94.795 | 94.795 | 94.495 | 94.495 | 94.79 | 94.79 | 94.49 | 94.49 |
| total | 100.00% | 100.00 g | 100.00% | 100.00 g | 100.00% | 100.00 g | 100.00% | 100.00 g |

The sodium hyaluronate was supplied by LIFECORE (CHASKA, Minn.). The Gantrez S-96 was supplied by ASHLAND (WILMINGTON, Del.). Polyquaternium 42 was supplied as Polyquaternium 42 (33% aqueous) by DSM BIOMEDICAL, (BERKELEY, Calif.). Polyquaternium 10 was supplied by ALDRICH CHEMICALS (ST. LOUIS, Mo.). The tartaric acid was supplied by AMRESCO (SOLON, Ohio).

The procedure for preparing Solutions 10A and 10C was as follows:
1. To each of 2 beakers was poured 50.00 grams of a 0.4% Sodium Hyaluronate Solution which was prepared by adding 249 grams of water into a separate container and slowly adding 1 gram of Sodium Hyaluronate into the water. The solution was mixed for 2 hours at ambient temperature to disperse the Sodium Hyaluronate. Additional water was added to bring the total amount of the solution to 94 grams and the solution is mixed an additional 10 minutes.
2. To each beaker solution was added 5 grams of Tartaric acid and mixed for 5 minutes to thoroughly dissolve the acid.
3. A total of 0.015 gram of Polyquaternium 42 is added to the solution of one of the beakers above while mixing.
4. The solution of step 3 is brought to 100 g using purified water and mixed for 5 minutes.
5. To the solution in the remaining beaker was added 0.01 gram of Polyquaternium 10 while mixing.
6. The solution prepared in step 5 was brought to 100 g using purified water and mixed for 10 minutes.

The procedure for preparing Solutions 10B and 10D was as follows:

1. Into a beaker containing 110.00 grams of water was slowly added 7.7 gram of a 13% solution of Gantrez S-96 as supplied.
2. The solution was mixed for 5 minutes to uniformly dissolve.
3. To the solution of step 2 was added 10.0 grams of Tartaric acid and mixed to dissolve.
4. Half of the solution of step 3 was separated for use as described in step 10.
5. To the remaining solution of step 3 was added 0.015 grams of Polyquaternium 42 while mixing.
9. The solution in step 5 was brought to 100 g using purified water and mixed for 5 minutes.
10. To the separated solution of step 4 was added 0.01 gram of Polyquaternium 10 while mixing.
11. The solution was brought to 100 g using purified water and mixed for 10 minutes.

Solutions 10A, 10B, 10C, and 10D containing the L-tartaric acid as the organic acid are clear and colorless with no precipitation evident. The L-tartaric acid used in this example had a solubility from Table 1 of >100 g/100 ml of water (at 25° C.)—or a solubility greater than the 10 g/100 ml threshold solubility (at 25° C.) for organic acids useful in the present invention.

Example 11: Solution with Anionic Polymer and Polyquaternium

Solutions were prepared containing both and anionic polymer (Sodium Hyaluronate or Gantrez S-96) and a Polyquaternium (PQ42 or PQ10). Table 12 shows the list of ingredients for solutions 11A-11D.

TABLE 12

Example 11 components.

| INGREDIENT | 11A % w/w | 11A amount per batch (gms) | 11B % w/w | 11B amount per batch (gms) | 11C % w/w | 11C amount per batch (gms) | 11D % w/w | 11D amount per batch (gms) |
|---|---|---|---|---|---|---|---|---|
| Sodium Hyaluronate | 0.200 | 0.200 | — | — | 0.200 | 0.200 | — | — |

TABLE 12-continued

Example 11 components.

| INGREDIENT | 11A | | 11B | | 11C | | 11D | |
|---|---|---|---|---|---|---|---|---|
| | % w/w | amount per batch (gms) | % w/w | amount per batch (gms) | % w/w | amount per batch (gms) | % w/w | amount per batch (gms) |
| Gantrez S-96 | — | — | 0.5 | 0.5 | — | — | 0.5 | 0.5 |
| Polyquaternium 10 | 0.1 | 0.1 | — | — | 0.1 | 0.1 | — | — |
| Polyquaternium 42 | — | — | 0.005 | 0.005 | — | — | 0.005 | 0.005 |
| Acetic Acid | 45.0 | 45.0 | 45.0 | 45.0 | — | — | — | — |
| Glutaric Acid | — | — | — | — | 32.0 | 32.0 | 32.0 | 32.0 |
| Purified Water | 54.7 | 54.7 | 54.495 | 54.495 | 67.7 | 67.7 | 67.495 | 67.495 |
| total | 100.00% | 100.00 g | 100.00% | 100.00 g | 100.00% | 100.00 g | 100.00% | 250.00 g |

The sodium hyaluronate was supplied by LIFECORE (CHASKA, Minn.). The Gantrez S-96 was supplied by ASHLAND (WILMINGTON, Del.). Polyquaternium 42 was supplied as Polyquaternium 42 (33% aqueous) by DSM BIOMEDICAL, (BERKELEY, Calif.). Polyquaternium 10 was supplied by ALDRICH CHEMICALS (ST. LOUIS, Mo.). The acetic acid was supplied by AVANTOR (PHILLIPSBURG, N.J.). The glutaric acid was supplied by ALFA AESAR (WARD HILL, Mass.).

The procedure for preparing Solutions 11A was as follows:
1. Into a beaker was poured 50.00 grams of a 0.4% Sodium Hyaluronate Solution which was prepared by adding 2988 grams of water into a separate container and slowly adding 12 gram of Sodium Hyaluronate into the water. The solution was mixed for 2 hours at ambient temperature to disperse the Sodium Hyaluronate.
2. Next, 45 grams of acetic acid was added to the beaker while mixing to disperse and solubilize.
3. Next, 0.10 gram of Polyquaternium 10 was added and mixed for 5 minutes to dissolve.
4. The solution prepared in step 3 was brought to 100 g using purified water and mixed for 10 minutes.

The procedure for preparing Solutions 11C was as follows:
1. Into a beaker was poured 100.00 grams of a 0.4% Sodium Hyaluronate Solution which was prepared by adding 2988 grams of water into a separate container and slowly adding 12 gram of Sodium Hyaluronate into the water. The solution was mixed for 2 hours at ambient temperature to disperse the Sodium Hyaluronate.
2. Next, 64 grams of glutaric acid was added to the beaker while mixing to disperse and solubilize.
3. The temperature of the solution was 10.1° C. (due to the endothermic reaction in step 2) and the solution was heated to 25° C. while mixing.
4. To half of the solution in step 3 was added 0.10 gram of Polyquaternium 10.
5. The solution was brought to a weight of 100 grams using purified water and mixed for 10 minutes.

The procedure for preparing Solutions 11B was as follows:
1. Into a beaker containing 46.15 grams of water was slowly added 3.85 gram of a 13% solution of Gantrez S-96 as supplied.
2. The solution was mixed for 5 minutes to dissolve.
3. To the solution of step 2 was added 45.0 grams of acetic acid while mixing.
4. To the solution of step 3 was added 0.015 grams of polyquaternium-42 while mixing.
5. The solution of step 4 was brought to 100 grams using purified water and mixed for 10 minutes.

The procedure for preparing Solutions 11D was as follows:
1. Into a beaker containing 110.00 grams of purified water was slowly added 7.7 gram of a 13% solution of Gantrez S-96 as supplied.
2. The solution was mixed for 5 minutes to uniformly dissolve.
3. To the solution of step 2 was added 64.0 grams of glutaric acid resulting in a cold undissolved mixture at a temperature of 20° C.
4. The solution was heated to 25° C. and mixed to dissolve.
5. Half of the above solution is removed.
6. To the remaining solution of step 4 was added 0.015 grams of Polyquaternium-42 while mixing to dissolve.
7. The solution was brought to 100 grams using purified water and mixed 10 minutes to dissolve.

Solutions 11A, 11B, 11C, and 11D containing either the glutaric or acetic acids as the organic acid are clear and colorless with no precipitation evident. The glutaric or acetic acids used in this example had solubilities from Table 1 of 63.9 and >100 g/100 ml of water (at 25° C.), respectively—or solubilities greater than the 10 g/100 ml threshold solubility (at 25° C.) for organic acids useful in the present invention.

Example 12: Solution with Anionic Polymer and Polyquaternium

Solutions were prepared containing both and anionic polymer (Sodium Hyaluronate or Gantrez S-96) and a Polyquaternium (PQ42 or PQ10). Table 13 shows the list of ingredients for solutions 12A-12D.

TABLE 13

Example 12 components.

| INGREDIENT | 12A % w/w | 12A amount per batch (gms) | 12B % w/w | 12B amount per batch (gms) | 12C % w/w | 12C amount per batch (gms) | 12D % w/w | 12D amount per batch (gms) |
|---|---|---|---|---|---|---|---|---|
| Sodium Hyaluronate | 0.2 | 0.2 | — | — | 0.2 | 0.2 | — | — |
| Gantrez S-96 | — | — | 0.5 | 0.5 | — | — | 0.5 | 0.5 |
| Polyquaternium 10 | — | — | — | — | 0.01 | 0.01 | — | — |
| Polyquaternium 42 | 0.005 | 0.0005 | 0.01 | 0.01 | — | — | 0.005 | 0.005 |
| Citric Acid | 30.0 | 30.0 | 15.0 | 15.0 | 20.0 | 20.0 | 15.0 | 15.0 |
| Purified Water | 69.795 | 69.795 | 84.49 | 84.49 | 79.79 | 79.79 | 84.495 | 84.495 |
| total | 100.00% | 100.00 g | 100.00% | 100.00 g | 100.00% | 100.00 g | 100.00% | 100.00 g |

The sodium hyaluronate was supplied by LIFECORE (CHASKA, Minn.). The Gantrez S-96 was supplied by ASHLAND (WILMINGTON, Del.). Polyquaternium 42 was supplied as Polyquaternium 42 (33% aqueous) by DSM BIOMEDICAL, (BERKELEY, Calif.). Polyquaternium 10 was supplied by ALDRICH CHEMICALS (ST. LOUIS, Mo.). The citric acid anhydrous was supplied by VWR/BDH (WEST CHESTER, Pa.).

The procedure for preparing Solutions 12A and 12C was as follows:
1. To each of 2 beakers was poured 50.00 grams of a 0.4% Sodium Hyaluronate Solution which was previously prepared by adding 249 grams of purified water into a separate container and slowly adding 1 gram of Sodium Hyaluronate into the water and mixed for 2 hours at ambient temperature to disperse the Sodium Hyaluronate.
2. To the solution of one of the beakers of was added 30 grams of citric acid and mixed thoroughly to dissolve the acid.
3. A total of 0.015 gram of Polyquaternium 42 was added to the solution in step 2 above while mixing.
4. The solution of step 3 was brought to 100 g using purified water and mixed for 5 minutes.
5. To the solution of the remaining beaker was added 20 grams of citric acid and mixed thoroughly to dissolve the acid.
6. To the solution of step 5 was added 0.01 gram of Polyquaternium 10 while mixing.
7. The solution prepared in step 6 was brought to 100 g using purified water and mixed for 10 minutes.

The procedure for preparing Solutions 12B and 12D was as follows:
1. Into each of two beakers containing 70.00 grams of water was slowly added 3.85 gram of a 13% solution of Gantrez S-96 as supplied.
2. The solutions were mixed for 5 minutes to uniformly dissolve.
3. To each of the 2 beakers was added 15.0 grams of citric acid and, in each case, mixed to dissolve.
4. To solution of one of the beakers from step 3 was added 0.015 grams of Polyquaternium 42 while mixing.
5. The solution was brought to 100 g using purified water and mixed for 5 minutes.
6. To the solution of the remaining beaker from step 3 was added 0.01 gram of Polyquaternium 10 while mixing.
7. The solution was brought to 100 g using purified water and mixed for 10 minutes.

Solutions 12A, 12B, 12C, and 12D containing citric acid as the organic acid are clear and colorless with no precipitation evident. The citric acid used in this example had a solubility from Table 1 of 59.2 g/100 ml of water (at 25° C.)—or a solubility greater than the 10 g/100 ml threshold solubility (at 25° C.) for organic acids useful in the present invention.

Example 13: Solution with Anionic Polymer and Polyquaternium

Solutions were prepared containing both and anionic polymer (Sodium Hyaluronate or Gantrez S-96) and a Polyquaternium (PQ42 or PQ10). Table 14 shows the list of ingredients for solutions 13A-13D.

TABLE 14

Example 13 components.

| INGREDIENT | 13A % w/w | 13A amount per batch (gms) | 13B % w/w | 13B amount per batch (gms) | 13C % w/w | 13C amount per batch (gms) | 13D % w/w | 13D amount per batch (gms) |
|---|---|---|---|---|---|---|---|---|
| Sodium Hyaluronate | 0.2 | 0.2 | — | — | 0.2 | 0.2 | — | — |
| Gantrez S-96 | — | — | 0.5 | 0.5 | — | — | 0.5 | 0.5 |
| Polyquaternium 10 | 0.01 | 0.01 | 0.01 | 0.01 | — | — | — | — |

TABLE 14-continued

| | Example 13 components. | | | | | | | |
|---|---|---|---|---|---|---|---|---|
| | 13A | | 13B | | 13C | | 13D | |
| INGREDIENT | % w/w | amount per batch (gms) | % w/w | amount per batch (gms) | % w/w | amount per batch (gms) | % w/w | amount per batch (gms) |
| Polyquaternium 42 | — | — | — | — | 0.005 | 0.005 | 0.005 | 0.005 |
| Succinic Acid | 4.0 | 4.0 | 3.0 | 3.0 | 3.0 | 3.0 | 4.0 | 4.0 |
| Purified Water | 95.79 | 95.79 | 96.49 | 96.49 | 96.795 | 96.795 | 95.495 | 95.495 |
| total | 100.00% | 100.00 g | 100.00% | 100.00 g | 100.00% | 100.00 g | 100.00% | 100.00 g |

The sodium hyaluronate was supplied by LIFECORE (CHASKA, Minn.). The Gantrez S-96 was supplied by ASHLAND (WILMINGTON, Del.). Polyquaternium 42 was supplied as Polyquaternium 42 (33% aqueous) by DSM BIOMEDICAL, (BERKELEY, Calif.). Polyquaternium 10 was supplied by ALDRICH CHEMICALS (ST. LOUIS, Mo.). The succinic acid was supplied by AMRESCO (SOLON, Ohio).

The procedure for preparing Solutions 13A and 13C was as follows:
1. To each of 2 beakers was poured 50.00 grams of a 0.4% Sodium Hyaluronate Solution which was previously prepared by adding 249 grams of purified water into a separate container and slowly adding 1 gram of Sodium Hyaluronate into the water and mixing for 2 hours at ambient temperature to disperse the Sodium Hyaluronate.
2. To the solution of one of the beakers was added 3 grams of succinic acid and mixed thoroughly to dissolve the acid.
3. A total of 0.015 gram of Polyquaternium 42 was added to the solution in step 2 above while mixing.
4. The solution was brought to 100 g using purified water and mixed for 5 minutes.
5. To the solution in the remaining beaker from step 1 was added 4 grams of succinic acid which is mixed thoroughly to dissolve the acid.
6. To the solution of step 5 was added 0.01 gram of Polyquaternium 10 while mixing.
7. The solution prepared in step 6 was brought to 100 g using purified water and mixed for 10 minutes.

The procedure for preparing Solutions 13B and 13D was as follows:
1. Into each of two beakers containing 86.15 grams of purified water was slowly added 3.85 gram of a 13% solution of Gantrez S-96 as supplied.
2. The each solution of step 1 was mixed for 5 minutes to uniformly dissolve.
3. To the solution of one of the beakers of step 2 was added 4.0 grams of succinic acid which is mixed to dissolve.
4. To the above solution in step 3 was added 0.015 grams of Polyquaternium 42 while mixing.
5. The solution of step 4 was brought to 100 g using purified water and mixed for 5 minutes.
6. To the solution of the remaining beaker from step 2 was added 0.01 gram of Polyquaternium 10 while mixing.
7. The solution of step 6 was brought to 100 g using purified water and mixed for 10 minutes.

Solutions 13A, 13B, 13C, and 13D containing the succinic acid as the organic acid are visually observed and noted to have precipitation. The succinic acid used in this example had a solubility from Table 1 of 8 g/100 ml of water (at 25° C.)—or a solubility less than the 10 g/100 ml threshold solubility (at 25° C.) for organic acids useful in the present invention.

What is claimed is:

1. A method of reducing the precipitation of a polyquaternium compound and an anionic polymer in a composition ophthalmologically suitable for application to the eyes comprising such compounds, comprising the steps of:
   i) providing from about 0.001% to about 0.5% of an anionic polymer having a weight average molecular weight of from about 250 to about 4,000,000 Daltons;
   ii) adding an effective amount of an organic acid, salts thereof or mixtures thereof, such that the organic acid binds with the monomer units of the polyquaternium compound at at least a 1:1 molar ratio; and
   iii) adding from about 10 ppm to about 1000 ppm of a polyquaternium compound having a weight average molecular weight of from about 150 to about 15,000 Daltons;
wherein the composition is substantially free of cationic oligomer compounds and precipitation inhibiting compounds.

* * * * *